United States Patent
King et al.

(10) Patent No.: US 9,187,351 B2
(45) Date of Patent: *Nov. 17, 2015

(54) WATER TREATMENT

(75) Inventors: Joseph A. King, Wayzata, MN (US);
John E. Hill, Plymouth, MN (US)

(73) Assignee: KING TECHNOLOGY INC., Hopkins, MA (US)

( * ) Notice: Subject to any disclaimer, the term of this patent is extended or adjusted under 35 U.S.C. 154(b) by 930 days.

This patent is subject to a terminal disclaimer.

(21) Appl. No.: 12/925,661

(22) Filed: Oct. 26, 2010

(65) Prior Publication Data

US 2011/0094972 A1    Apr. 28, 2011

Related U.S. Application Data

(60) Continuation of application No. 12/386,109, filed on Apr. 14, 2009, and a continuation of application No. 12/001,351, filed on Dec. 11, 2007, and a continuation-in-part of application No. 12/315,285, filed on Dec. 2, 2008, now Pat. No. 7,875,191, which is a continuation of application No. 11/999,654, filed on Dec. 6, 2007, now Pat. No. 7,501,067, which is a division of application No. 10/928,668, filed on Aug. 26, 2004, now Pat. No. 7,347,934.

(60) Provisional application No. 61/279,859, filed on Oct. 27, 2009, provisional application No. 61/126,105, filed on May 8, 2008, provisional application No. 60/878,016, filed on Dec. 29, 2006.

(51) Int. Cl.
*C02F 1/50* (2006.01)
*A01N 59/16* (2006.01)
*C02F 1/76* (2006.01)
*C02F 1/68* (2006.01)

(52) U.S. Cl.
CPC . *C02F 1/50* (2013.01); *A01N 59/16* (2013.01); *C02F 1/505* (2013.01); *C02F 1/688* (2013.01); *C02F 1/76* (2013.01)

(58) Field of Classification Search
CPC ............ C02F 1/50; C02F 1/505; C02F 1/683; C02F 1/76; C02F 1/766; C02F 103/42; C02F 1/68; C02F 1/08; A01N 59/16
See application file for complete search history.

(56) References Cited

U.S. PATENT DOCUMENTS

| 5,888,428 A * | 3/1999 | Howarth et al. ............... 252/403 |
| 2006/0043011 A1 * | 3/2006 | King et al. .................. 210/198.1 |
| 2008/0156739 A1 * | 7/2008 | King ............................ 210/749 |

* cited by examiner

*Primary Examiner* — Lucas Stelling
(74) *Attorney, Agent, or Firm* — Jacobson & Johnson LLC

(57) ABSTRACT

A sanitizing agent for maintaining a biocidal effective bacteria count in a body of water comprising a metal ion donor for donating a metal ion and a compound containing a hydantoin ring with the combination of the compound containing the hydantoin ring with the metal ion donor enhancing the effectiveness of the sanitizing agent to enable the sanitizing agent to maintain a biocidal effective bacteria count in the body of water.

12 Claims, 4 Drawing Sheets

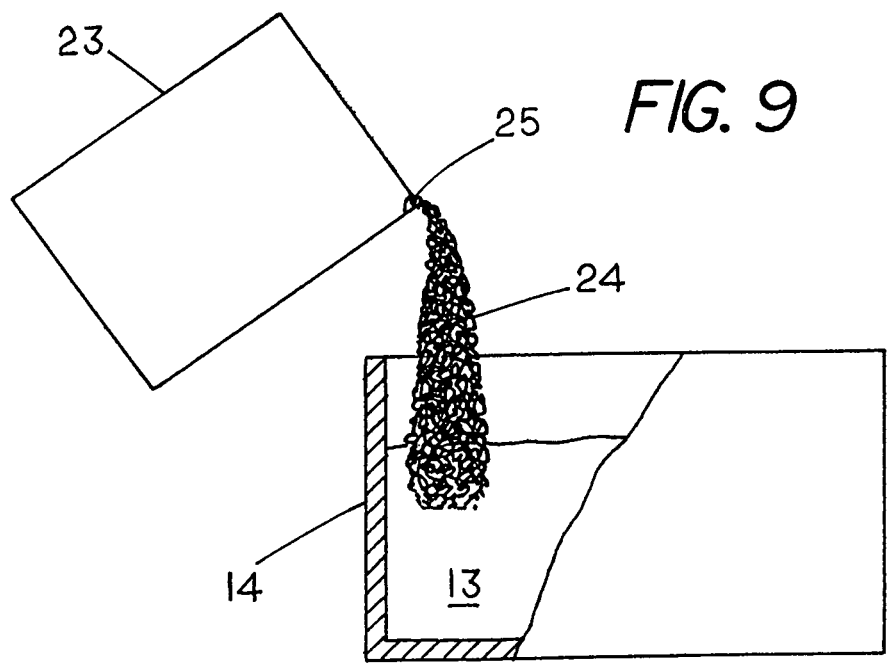
FIG. 9
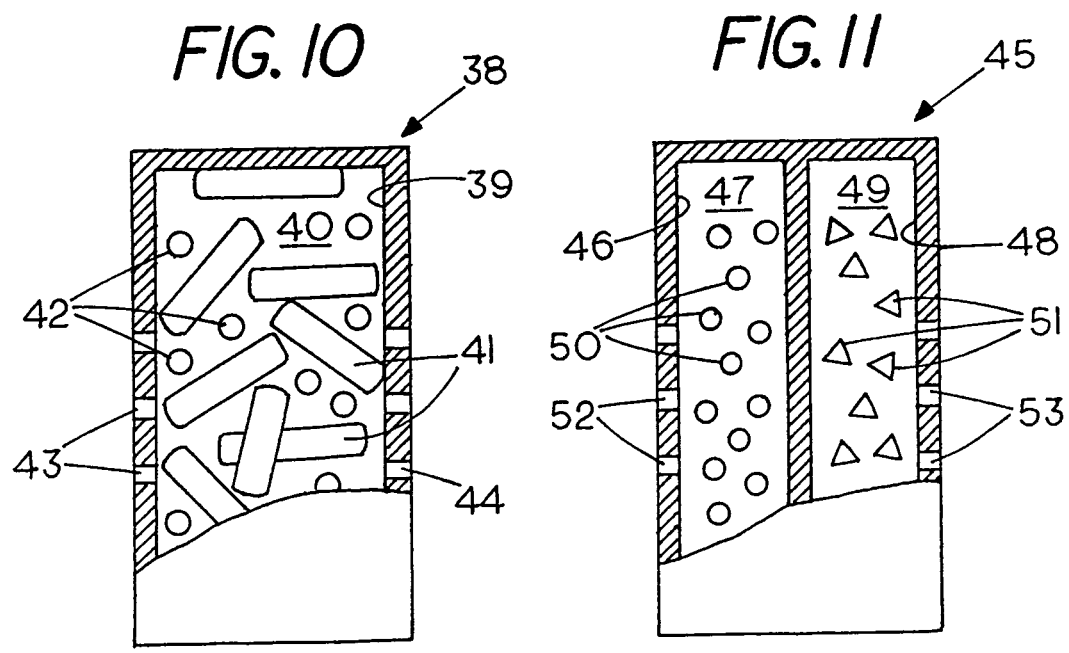
FIG. 10
FIG. 11

WATER TREATMENT

CROSS REFERENCE TO RELATED APPLICATIONS

This application claims priority from provisional application Ser. No. 61/279,859 filed Oct. 27, 2009 entitled Enhanced Disinfectant; is a continuation of Ser. No. 12/386,109 filed Apr. 14, 2009, which claims priority from provisional application Ser. No. 61/126,105 filed May 8, 2008, is a continuation of application Ser. No. 12/001,351 filed Dec. 11, 2007 entitled Ion Enhancement (now abandoned), which claims priority from provisional application Ser. No. 60/878,016 filed Dec. 29, 2006 entitled Ion Enhancement; and is a continuation-in-part of application Ser. No. 12/315,285 filed Dec. 2, 2008 entitled Biocide (now U.S. Pat. No. 7,875,191), which is a continuation of application Ser. No. 11/999,654 filed Dec. 6, 2007 (now U.S. Pat. No. 7,501,067), which is a division of patent application Ser. No. 10/928,668 filed Aug. 26, 2004 entitled Biocide (now U.S. Pat. No. 7,347,934).

FIELD OF THE INVENTION

This invention relates generally to water treatment and, more specifically, to water treatment with a sanitizing agent having a compound containing a hydantoin ring where the sanitizing agent may be in solid form.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of treating water with of metallic ions to kill bacteria in a body of water is known in the art. Metallic ions such as copper, zinc or silver ion are an effective bactericide for a body of water including recreational water, which can be defined as water that is not intended for consumption/drinking purposes and may include but are not limited to water in swimming pools, spas, jetted tubs, hot tubs or the like. Metallic ions are oftentimes a preferred sanitizing material because they are generally easier and safer to use than other known bactericides or algaecides. A further advantage of using a metal ion such as silver ion as a bactericide is that silver ion minimizes the need for pH adjustment of the body of water. However, if the concentration of metallic ions such as silver ions in a body of water is too low the ability to kill microorganisms is reduced or lost. On the other hand if the concentration of metallic ions such as silver ions is too high it can be harmful to those who use the body of water. Thus when silver ion is used as a disinfectant in a body of water one generally want to maintain the concentration of the silver ion in an effective range to kill microorganisms.

The concept of introducing biocidal metals into a body of water to generate biocidal metal ions, such as silver ions, to sanitize the body of water is known in the art. The use of these ions to purify the body of water results in decreased need for chlorination. An example of a method of introducing biocidal metal ions into water involves the use of sacrificial electrodes containing metals corresponding to the desired ions, including alloys of silver and copper, and electrolytically dissolving the metals into the water. Other methods of introducing biocidal metal ions into water include contacting the water with substrates that have been coated or impregnated with pure or alloyed metal, soluble metal salts, or some combination thereof.

Traditionally, the sources of metallic ions used to kill bacteria in recreational water have been limited to metallic ion donors that are readily soluble in the recreational water in order to maintain an effective concentration of the biocides in the body of water. Silver chloride (AgCl), for example, has been a commonly used bactericide for releasing silver ions into the body of water to effectively kill microorganisms. Sodium bromide has also been known to be used with silver chloride to provide an additional and alternative water disinfection system.

SUMMARY OF THE INVENTION

A sanitizing agent for maintaining a biocidal effective bacteria count in a body of water comprising a metal ion donor for donating a metal ion and a compound containing a hydantoin ring with the combination of the compound containing the hydantoin ring with the metal ion donor enhancing the effectiveness of the sanitizing agent to enable the sanitizing agent to maintain a biocidal effective bacteria count in the body of water where the sanitizing agent may be added to the body of water in solid or nonsolid form.

BRIEF DESCRIPTION OF THE DRAWINGS

FIG. 9 shows the DMH/silver based liquid sanitizer of FIG. 7 being dispensed through an orifice of a dispenser container into a body of water;

FIG. 10 shows an example of a one chamber dispenser; and

FIG. 11 shows an example of a two-chamber dispenser.

DESCRIPTION OF THE PREFERRED EMBODIMENT

Figure 1:
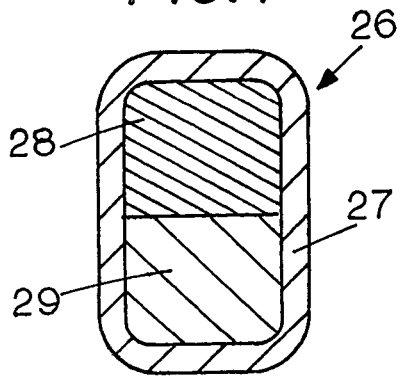
FIG. 1 shows a tablet that provides for the in situ formation of the DMH/Ag complex for disinfecting a body of recreational water.

Hydantoin and its derivatives, also known as glycolyurea, is an imidazole analogue. It is a heterocyclic compound having two ketone groups in a five-membered ring structure composed of three carbon atoms and two nitrogen atoms at nonadjacent positions. It is a white crystalline compound; slightly soluble in water; melting at 222 C. Hydantoin and its derivatives have a variety of uses including in the preparation of textile softeners, lubricants, resins, and agrochemicals. Some hydantoins have bacteriostatic and bactericidal capabilities, which are useful preservatives against bacteria and fungi. They have antibacterial, antifungal, antiprotozoal, and anthelmintic activity and are used in manufacturing pharmaceuticals especially anticonvulsant drugs such as phenytoin, ethotoin, and methyphenytoin while others lack any biocidal properties.

Halogens such as chlorine and bromine are often used either alone or in combination with other biocides in order to reduce the level of chlorine and bromine since high levels of halogens such as chlorine and bromine can create an unpleasant water environment. To reduce the levels of chlorine or bromine one may use supplemental sanitizing agents such as metal ions with the halogens, which allows one to reduce the levels of halogen in the body of water while still maintaining a biocidal effective bacteria count in the body of water. However, in some cases the level of halogens may still be unpleasant. A feature of the invention described herein is that a level of halogens in the body of water can be reduced even further through the addition of a compound containing a hydantoin ring even though the compound having the hydantoin ring lacks any independent biocidal properties. That is, the compound containing the hydantoin ring when used alone in the body of water would be ineffective in killing harmful organisms in a body of water.

To sanitize a body of water one may use a metal ion donor for donating a metal ion wherein the level of halogen and the concentration of metal ions in combination is used reduce the bacteria count in the body of water but the bacteria or microorganism reduction is insufficient with the combination is insufficient to render the body of water safe for usage for the intended purpose. Thus, while the level of halogen becomes less offensive the bacteria count reduction in effect only maintains a bacteria ineffective count in the body of water. That is, the level of halogen and the level of metal ions while effective in reducing the number of microorganisms, may be unable to reduce the number of microorganisms in a body of water to a safe level during a specified time. The acceptable number of microorganisms i.e. the biocidal effective bacteria count in the body of water which may include the time required to kill or reduce harmful microorganisms is typically established by tests, usually by a governmental agency or other recognized body, which is concerned with consumer safety. By adding a compound containing a hydantoin ring to the body of water, which is sanitized with a halogen and a source of metal ions that normally results in a bacteria ineffective count in the body of water, the halogen metal ion donor combination with the compound containing the hydantoin ring can enhance or increase the level of the metal ions in the body of water thus enhancing the effectiveness of the sanitizing agent to a point that enables the sanitizing agent to maintain a biocidal effective bacteria count, which is less than the first bacteria ineffective count that was generated by the halogen and the metal ion donor without the compound containing the hydantoin ring.

One of the problems associated with the use of metal ions such as silver ions for killing microorganisms is that silver has a tendency to complex with other compounds and become increasingly insoluble thereby reducing the effective microorganism killing ability of the silver. For example, it would not be anticipated that silver chloride when used in combination with sodium bromide would be an effective disinfectant system because of the combination's tendency to form insoluble bromide crystals, which are not believed to be biologically active in aqueous environments. However, it has been discovered that if silver forms a complex or association with hydantoins, the silver will remain soluble to a higher degree thereby retaining the silver's antimicrobial activity.

Hydantoin structures are also known as complexing agents in silver-plating processes (R. J. Morrissey, U.S. Patent Application Publication no. 2005/0183961). Studies performed by the inventors have demonstrated that halogeneated hydantoins such as Bromochlorodimethylhydantoin (BCDMH) and Dichlorodimethylhydatoin (DCDMH) tend to increase levels of dissolved silver when used in conjunction with a source of silver. While not fully understood it is believed that the aforementioned increased in solubility is due to a soluble complex or association between silver and hydantoin ring structures since it has been found the silver remains soluble to a higher degree than expected thus making more silver ions available for killing harmful microorganism.

DMH is a chemical derivative of hydantoin comprising of a hydantoin ring with two methyl groups attached at the number five position of the ring. DMH is a component of Bromochlordimethyl hydantoin (BCDMH), organic source bromine utilized for disinfecting spa water. Research performed by the Applicant has shown that when BCDMH is combined with silver ions in spa water, levels of dissolved silver are higher than would be anticipated for water containing bromine. Additional research performed by the Applicant seems to indicate that the DMH portion of the BCDMH molecule alone may be responsible for the increased solubility of silver. The mechanism of increased silver solubility appears to involve the formation of a DMH/silver complex that has a higher solubility in water than silver salts such as silver bromine or silver chloride. It is should be noted that the antimicrobial activity tends to increase with soluble silver concentration. A second possible mechanism is that silver, of a given concentration, has more antimicrobial activity as a DMH complex than a comparable concentration of silver alone. One possible mechanism is that the DMH/silver complex is more readily delivered to target organisms, resulting more effective killing.

The applicant has discovered various options for utilizing DMH/silver complexes and compounds containing a hydantoin ring for use in sanitizing mediums including surfaces objects a body of water which may include swimming pool, spas, and hot tubs. More specifically, the use of a compound having a hydantoin ring has been found to enhance the effectiveness of metal ions when used in a body of water thereby reducing the required level of chlorine necessary to maintain the body of water at biocidal effective levels.

One of the options for utilizing DMH/silver complexes in treating a body of water such as a body of recreational water is to add DMH and silver to the body of water separately and allow DMH and silver to form a complex in situ. In the in situ environment, DMH behaves as an adjuvant. An adjuvant is defined as a substance that has few or no effects alone, but increases the efficacy or potency of another substance, in this case silver. Results of the Applicant's testing reveals that the DMH/silver complexes formed in situ provides for greater antimicrobial activity compared to the equivalent level of silver used alone.

Although DMH/silver complexes formed in situ provides for desired antimicrobial activity in various applications, the inventor has discovered that when certain additives such as reduced levels of halide and/or other chemicals are used with the DMH/silver complex in treating a body of water, the additives, by themselves or in combination, function to increase the efficacy of the antimicrobial activity of the DMH/silver complex to levels that exceed disinfection goals for recreational waters such as swimming pools, spas, and hot tubs. An example of the possible disinfection goals may comprise the DMH/silver complex providing at least a 6.0 log reduction in microorganism numbers within 0.5 minutes for *E. coli* and at least a 6.0 log reduction in microorganism numbers within 2.0 minutes for *E. Faecium* in the body of recreational water. Examples of such additives include but are not limited to low levels of chlorine (0.1-0.25 ppm chlorine), Enzymes, Surfactants, Biguanides, Hydrogen peroxide, and Potassium monopersulfate.

Another option for utilizing DMH/Ag complex in treating a body of water is to synthesize the DMH/silver complex under controlled conditions instead of in situ. One method in synthesizing the DMH/Ag complex is to make the DMH/Ag complex where a single silver atom is quantitatively attached to a DMH molecule. An example of such a process involves mixing silver nitrate together with DMH under highly basic conditions followed by a filtration wash. Formation of the complex may be confirmed by laboratory analysis.

In testing the synthesized DMH/Ag complex, a single microbiological assay of the antimicrobial activity of the synthesized DMH/Ag complex reveals that the synthesized DMH/Ag complex has the potential to control microbial growth without the need for an added source of halide. Similar to the DMH/Ag complex formed in situ, results of the Applicant's testing reveals that the synthesized DMH/Ag complex at the very least provides for greater antimicrobial activity compared to the antimicrobial activity for the equivalent level of silver used alone.

Although testing of the synthesized DMH/Ag complex indicates that the synthesized DMH/Ag complex provides for desired antimicrobial activity in various applications, the inventor has further discovered that when certain additives such as reduced levels of halide and/or other chemicals are used with the synthesized DMH/Ag complex in treating a body of water, the additives also function to increase the efficacy of the antimicrobial activity of the DMH/Ag complex to levels that exceed disinfection goals for recreational waters such as swimming pools, spas, and hot tubs.

As an alternative option to adding additives with the synthesized DMH/Ag complex to increase the efficacy of the antimicrobial activity of the DMH/Ag complex in treating a body of water, a third component such as a halide may be synthesized directly to the DMH to for DMH/Ag/halide complex.

The following is an example of a compound having a hydantoin ring:

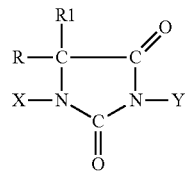

Where X is either Ag or Cl;
Y is Ag if X is Cl or Y is Cl if X is Ag;
R is a hydrogen or a methyl group; and
R1 is a hydrogen or a methyl group.

As an example, the synthesized DMH/Ag/Cl complex may be form by synthesizing DMH/Ag and synthesizing Chloro-DHM/Ag from DCDMH.

It is noted that the synthesized DMH/Ag complex and the synthesized DMH/Ag/Cl complex may be use in various forms including but not limited to liquids, granulars, powders and tablets. In an alternative embodiment, X may also be either Ag, Cl, or Br
Y may also be either Ag, Cl, or Br;
R is an Alkyl group; and
R1 is an Alkyl group For example, the above may result in the formation the following structures:

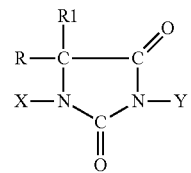

1-silver-3-chloro-5,
5-dimethyl hydantoin

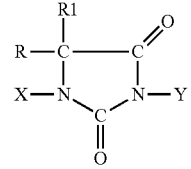

1-silver-3-bromo-5,
5-dimethyl hydantoin

Although silver and chloride may be obtained from a variety of sources, an example of the source of silver and chloride discussed hereafter will be in the form of silver chloride (AgCl). Silver chloride is a white powder that can be melted or cast like a metal, and is generally derived from heating a silver nitrate solution and adding hydrochloric acid or salt solution to produce a silver chloride solution, which is then boiled or filtered either in the dark or under a ruby red light to produce the silver chloride powder.

FIGS. 1, 1A, 1B, 1C, and 1D each show an embodiment of a stand-alone disinfectant tablet. Referring to FIG. 1, FIG. 1 shows a stand-alone disinfectant tablet 26 that provides for the in situ formation of the DMH/Ag complex for disinfecting a medium including a body of water which may be recreational water such as a swimming pool, spa or hot tub. Tablet 26, as shown in FIG. 1, generally comprises an outer layer of a silver ion donor such as silver chloride 27 encapsulating an inner core which may contain additional silver 28 to provide for a source of silver ions and a compound 29 having a hydantoin ring, for example compounds such as DMH or BCDMH (Bromochlorodimethylhydantoin) although others may be used as described herein The source of silver 28 ions may be silver chloride or other various sources such as for example elemental silver, various types of silver alloys, silver oxide, silver salt, or some combination thereof. The silver may be used standing along in its pure/elemental or alloyed form or coated or impregnated to a substrate. The silver may be introduced into the water through the dissolution of silver nitrate, or through the dissolution of metallic silver as the result of conversion to silver oxide and subsequent conversion of the oxide to more soluble silver species. In addition, various insoluble or slightly soluble transition metal salts may be used in the present invention as a source of silver. Examples of insoluble or slightly soluble transition metal salts suitable for use as silver ion donors in the tablet include, but are not limited to, AgCl, AgBr, AgI, $Ag_2S$, $Ag_3PO_4$, $NaAg_2PO_4$, CuS, and $NaCuPO_4$. Other examples of silver compounds include, but are not limited to, $AgNO_3$, $Ag_2CO_3$, AgOAc, $Ag_2SO_4$, $Ag_2O$, $[Ag(NH_3)_2]Cl$, $[Ag(NH_3)_2]Br$, $[Ag(NH_3)_2]I$, $[Ag(NH_3)_2]NO_3$, $[Ag(NH_3)_2]_2SO_4$, silver acetoacetate a silver benzoate, a silver carboxylate, silver amine complexes such as $[Ag(NR_3)_2]X$, where R is an alkyl or aryl group or substituted alkyl or aryl group and X is an anion such as, but not limited to, $Cl^-$, $Br^-$, $I^-$, $OAc^-$, $NO_3^-$ and $SO_{16}^-$.

In the example of FIG. 1 the layer of silver chloride 27 releases silver ions and chloride ions into the body of water to effectively kill or control an initial population of microorganisms. A compound containing a hydantoin ring 29 such as BCDMH or DMH provides a hydantoin ring and the silver 28 provides the source of silver ions to the body of water. The hydantoin compound and the silver ions interact with each other to form, for example, a DMH/silver complex in situ in the body of water to provide for an effective prolonged sanitizer. The remaining chloride ions in the body of water function to help increase the efficacy of the antimicrobial activity of the DMH/silver complex to levels that exceed disinfection goals.

An example of one of the processes involved in forming the tablet 26 may comprise the combination of the silver chloride 27 while in solution with an adhesive to form an adhesive silver chloride solution. The adhesive and the silver chloride solution are then applied to the surface of a carrier containing the silver 28 and the compound 29 having a hydantoin ring such as BCDMH. A suitable material for adhesively securing the silver chloride 27 proximate the carrier is commercially available gelatin, which can be cross-linked with an aqueous solution of formaldehyde or glutaraldehyde to form a non-soluble, water penetrable matrix on the exterior surface of the carrier. Other suitable non-soluble water porous adhesive matrixes are polyvinyl acetate, polyurethane, epoxy resin, polyvinyl alcohol and polyvinyl acetate.

Figure 1A:
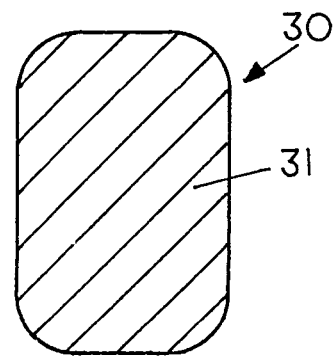
FIG. 1A shows a tablet comprising a synthesized DMH/Ag/Cl complex.
Figure 1B:
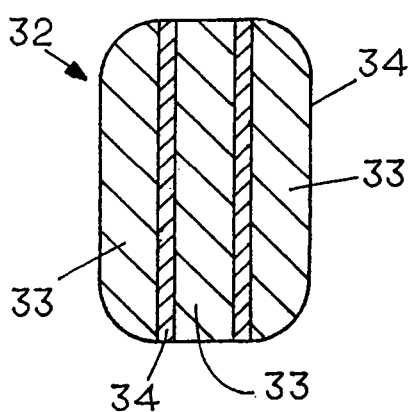
FIG. 1B shows a tablet comprising multiple layers of silver chloride and multiple layers of the synthesized DMH/Ag complex.
Figure 1C:
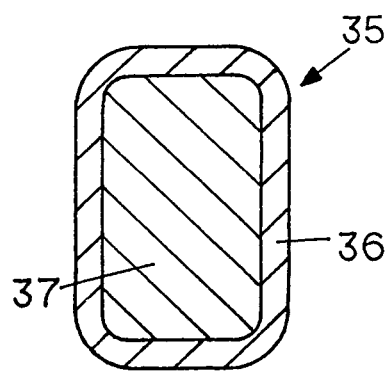
FIG. 1C shows a tablet comprising the synthesized DMH/Ag/Cl complex encapsulated by a layer of silver chloride.
Figure 1D:
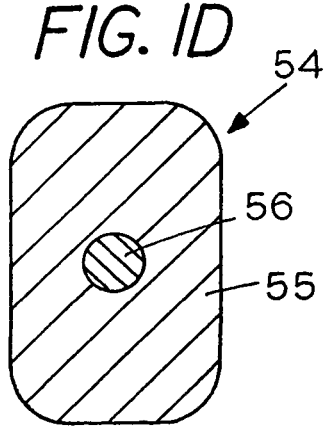
FIG. 1D shows a stand-alone disinfectant tablet comprising a source of synthesized DMH/Ag complex having a source of silver chloride situated at the center of the tablet.

FIG. 1A shows a stand-alone disinfectant tablet 30 for treating an open bodying of water comprising a synthesized DMH/Ag/Cl complex 31 wherein the source of metal ions and a compound containing the hydantoin ring are intermixed in the tablet. FIG. 1B shows a stand-alone disinfectant tablet 32 comprising multiple layers of silver chloride 34 and multiple layers of the compound containing the hydantoin ring 33. FIG. 1C shows a stand-alone disinfectant tablet 35 encapsulated by a layer of silver chloride 36. FIG. 1D shows a stand-alone disinfectant tablet 54 having a source of silver chloride 56 situated at proximal the center of the source of synthesized DMH/Ag complex 55. Thus as shown in FIGS. 1, 1B and 1C the tablet is a layered tablet wherein the source of metal ions comprises a layer of a source of silver ions with the layer of the source of silver ions either encapsulating an exterior surface of the layered tablet (FIG. 1) or forming an intermediate layer having an exposed end (FIG. 1B) to provide a gradual release of silver ions. A source of silver ions has been described but other biocidal metal ions such as for example zinc and copper may be used. A halogen such as chlorine in either a liquid, a solid, a gas or combinations thereof may be used in conjunction with the tablets and if chlorine is in tablet form the chlorine tablet and the disinfectant tablet may be combined as a single tablet.

Figure 2:
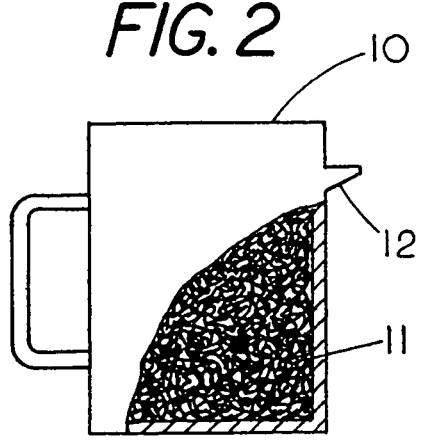
FIG. 2 shows a DMH and silver chloride powder for forming a DMH/Ag complex in situ an a medium such as an open body of water.

FIG. 2 shows an embodiment of using a stand-alone disinfectant DMH/silver complex based powder or granules located in a dispenser container 10 which supports a pourable mixture of DMH and silver chloride 11 in powder or granular form therein. In the powder or granular form, the DMH and silver chloride do not interact with each other to form the DMH/silver complex. Instead the DMH/silver complex is formed in situ, that is the interaction between the DMH and silver chloride is initiated once the DMH and silver chloride comes in contact with a fluid source, such as recreational water from a swimming pool, spa, or hot tub or other types of nonrecreational water. Thus the above described examples show that the solid may be in granular or powder form (FIG. 2) or in tablet form with the source of silver ions and the compound containing the hydantoin ring either in an intermixed condition as shown in FIG. 1A or structurally isolated from each other as shown in FIG. 1, FIG. 1B, FIG. 1C and FIG. 1D. A feature of the invention is that it includes a method for maintaining a body of water in a sanitized condition by placing a solid in tablet or granular form in the body of water with the solid comprising a source of metal ions and a compound having a hydantoin ring wherein the release of the both the metal ions and the compound containing the hydantoin ring from the solid increases the level of metal ions to a level greater than if only the source of metal ions were present. While solids are shown as tablets where the compound containing the hydantoin ring and the source of metal ions are in a single tablet the source of silver ions may be separate tablet from the compound containing the hydantoin ring. Likewise, the source of metal ions may be in other forms for release into the body of water without departing from the spirit and scope of the invention.

Figure 3:
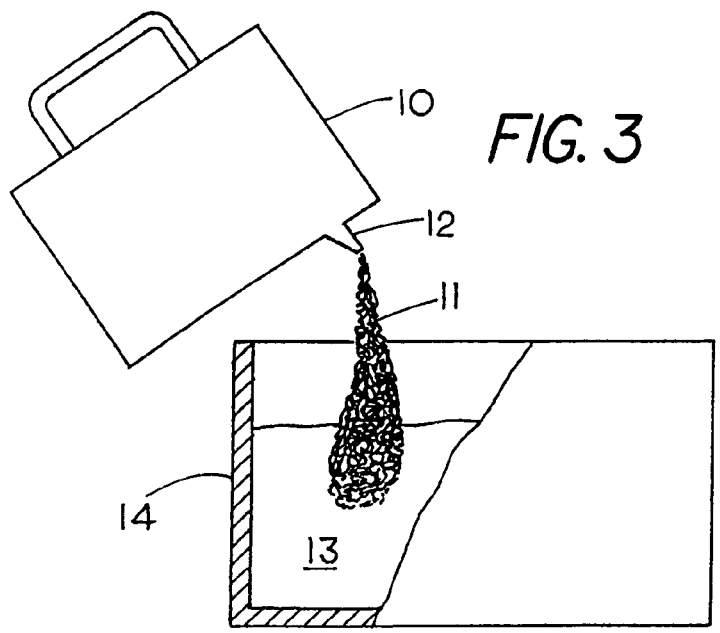
FIG. 3 shows the DMH and silver chloride powder of FIG. 1 being dispensed through a spout of a dispenser container into a body of water.

FIG. 3 shows the DMH and silver chloride powder mixture 11 being dispensed through a spout 12 of the dispenser container 10 into a body of water 13 supported by a housing 14. As the DMH and silver chloride mixture 11 comes into contact with the body of water 13, the silver chloride in the DMH and silver chloride mixture 11 releases silver ions and chloride ions into the body of water 13 to effectively kill or control the growth of microorganisms.

The DMH and the silver ions also interact with each other to form a DMH/silver complex to provide for an effective prolonged sanitizer. In addition, it has been found that the remaining chloride ions also function to help increase the efficacy of the antimicrobial activity of the DMH/silver complexes to levels that exceed disinfection goals.

It is noted that as an alternative to the DMH and silver chloride mixture 11, dispenser container 10 may alternatively support a mixture comprising the synthesized DMH/Ag complex and an additive such as silver chloride or the synthesized DMH/Ag/Cl complex alone.

Figure 4:
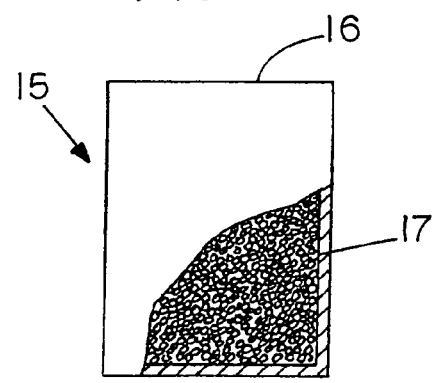
FIG. 4 shows granules sanitizer comprising particles of synthesized DMH/Ag complex and silver chloride supported in a container for sanitizing a medium.

FIG. 4 shows an embodiment of a stand-alone disinfectant DMH/silver based sanitizer 15 comprising a dispenser container 16 supporting granules or pellets 17 comprising particles of synthesized DMH/Ag complex and silver chloride therein. An example of one of the processes involved in forming pellets 17 comprise the combination of the silver chloride while in solution with an adhesive to form an adhesive silver chloride solution. The adhesive and the silver chloride solution are then applied to a carrier such as a pellet. The pellet may be an active carrier, such as containing the synthesized DMH/Ag complex, or a passive carrier, in which the synthesized DMH/Ag complex is added to the silver chloride solution as the adhesive is cured to produce a pellet coated with silver chloride particles and particles of synthesized DMH/Ag complex with both the silver chloride particles and particles of synthesized DMH/Ag complex available for releasing into the body of water 13 to initiate the disinfection process of the body of water 13. A suitable material for adhesively securing the silver chloride proximate the carrier is commercially available gelatin, which can be cross-linked with an aqueous solution of formaldehyde or glutaraldehyde to form a non-soluble, water penetrable matrix on the exterior surface of the carrier. Other suitable non-soluble water porous adhesive matrixes are polyvinyl acetate, polyurethane, epoxy resin, polyvinyl alcohol and polyvinyl acetate.

Figure 5:
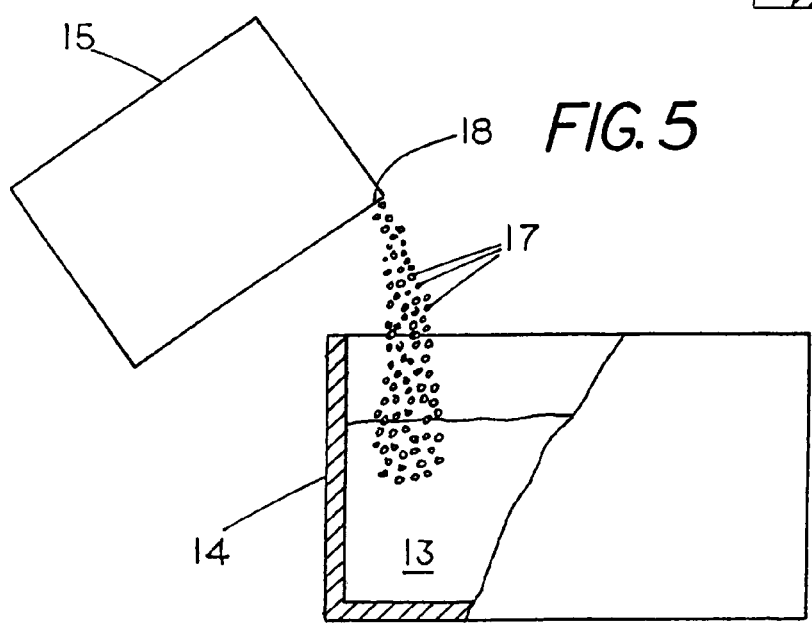
FIG. 5 shows the synthesized DMH/Ag complex and silver chloride granules sanitizer of FIG. 3 being dispensed into a body of water.

FIG. 5 shows the synthesized DMH/Ag complex and silver chloride pellets 17 being dispensed through an orifice 18 located on the dispenser container 16 into the body of water 13 supported by housing 14. As the synthesized DMH/Ag complex and silver chloride pellets 17 come into contact with the body of water 13, the silver chloride in the pellets 17 releases silver ions and chloride ions into the body of water 13 to effectively kill or control the growth of microorganisms. The synthesized DMH/Ag complex is also released to provide for an effective prolonged sanitizer. The inventor has discovered that the remaining chloride ions previously released into the body of water 13 also function to help increase the efficacy of the antimicrobial activity of the synthesized DMH/Ag complex to levels that exceed disinfection goals.

It is noted that as an alternative to the synthesized DMH/Ag complex and silver chloride pellets 17, dispenser container 16 may alternatively support granules or pellets comprising a synthesized DMH/Ag/Cl complex and an additive such as silver chloride therein.

A feature of synthesized DMH/Ag complex and silver chloride pellets 17 is that unlike the DMH and silver chloride powder or granular mixture 11 of FIGS. 2 and 3, the synthesized DMH/Ag complex and silver chloride pellets 17 releases the silver chloride and the synthesized DMH/Ag complex at a slower rate for a more time-controlled release. That is, the silver chloride and the synthesized DMH/Ag complex located inside or located in the inner layer of the synthesized DMH/Ag complex and silver chloride pellets 17 are not released, i.e. dissolved in the body of water until the synthesized DMH/Ag complex and silver chloride located on the outer layer of the pellets 17 are released into the body of water 13. Use of the synthesized DMH/Ag complex and silver chloride pellets 17 thus will be ideal for recreational waters such as in a pool, spa, or hot tub in which the same body of water is intended to be use repeatedly.

Figure 6:
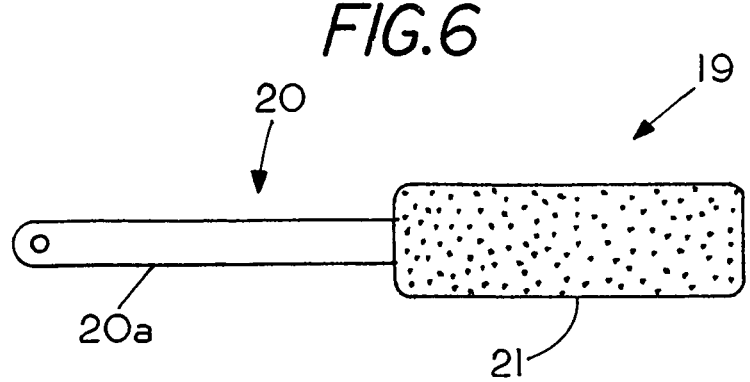
FIG. 6 shows a DMH/silver based sanitizing dipstick sanitizer for treating a medium such as a body of water.

FIG. 6 shows a stand-alone disinfectant DMH/silver based sanitizing dipstick 19 comprising a pad or puck 21 made up of synthesized DMH/Ag complex and silver chloride with pad or puck 21 having a handle 20a extending therefrom. The DMH/silver based sanitizing dipstick 19 may be formed similar to the synthesized DMH/Ag complex and silver chloride pellets 17 of FIGS. 4 and 5, namely by the combination of the silver chloride while in solution with an adhesive to form an adhesive silver chloride solution. The adhesive and the silver chloride solution are then applied to an end of a stick 20. The synthesized DMH/Ag complex may then be added to the silver chloride solution as the adhesive is cured to produce the synthesized DMH/Ag complex and silver chloride pad or puck 21 comprising silver chloride particles and particles of synthesized DMH/Ag complex with both the silver chloride particles and particles of synthesized DMH/Ag complex available for releasing into the body of water 13 to disinfect the body of water 13.

The cross-section for the DMH/silver based sanitizing dipstick 19 may be of any choice, e.g. square, rectangular, oval, hexagonal, irregular, etc. . . . . The synthesized DMH/Ag complex and silver chloride pad or puck 21 is utilized to dispense the silver chloride and synthesized DMH/Ag complex into any type of water source such as in a swimming pool, spa, or hot tub. Once exhausted, the DMH/silver based sanitizing dipstick 19 may be disposed of by simply discarding the stick 20. As an alternative to the synthesized DMH/Ag complex and silver chloride pad or puck 21, DMH/silver based sanitizing dipstick may include a pad or puck comprising the synthesized DMH/Ag/Cl complex alone. An advantage of the dipstick dispenser is that the sanitizing material may be removed from the body of water for reuse if sanitizing of the water is no longer required.

Figure 7:
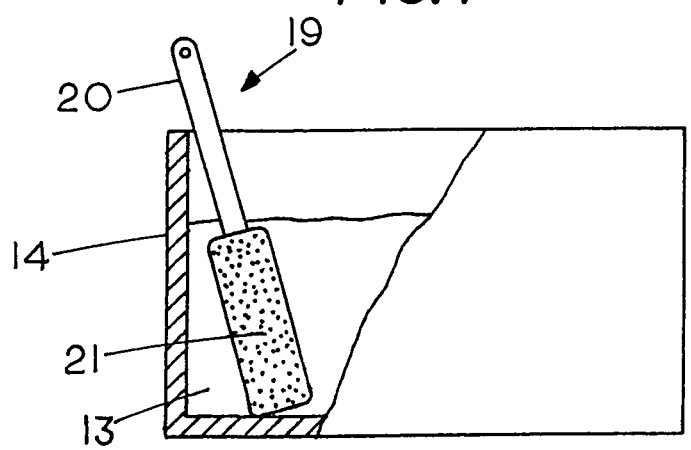
FIG. 7 shows the DMH/silver based sanitizing dipstick sanitizer of FIG. 5 being used in an open body of water.

FIG. 7 shows the stand-alone disinfectant DMH/silver based sanitizing dipstick 19 of FIG. 6 being used in housing 14 with at least a portion of the DMH-silver chloride pad 21 submerged in the body of water 13 to dispense the synthesized DMH/Ag complex and silver chloride into body of water 13. Since the pad 21 is thicker/has more volume than the pellets 17 of FIGS. 4 and 5, the pad 21 can have a longer life then the powder mixture 11 of FIGS. 2 and 3 and the pellets 17 of FIGS. 4 and 5. That is, the synthesized DMH/Ag complex and silver chloride located inside or located in the inner layer of the synthesized DMH/Ag complex and silver chloride pad 21 are not released, i.e. dissolved in the body of water, until the silver chloride and synthesized DMH/Ag complex located on the outer layer of the pad 21 are released into the body of water 13. Use of the DMH/silver based sanitizing dipstick 19 thus will be ideal for an open body of water that requires lengthy or extended sanitation.

Figure 8:
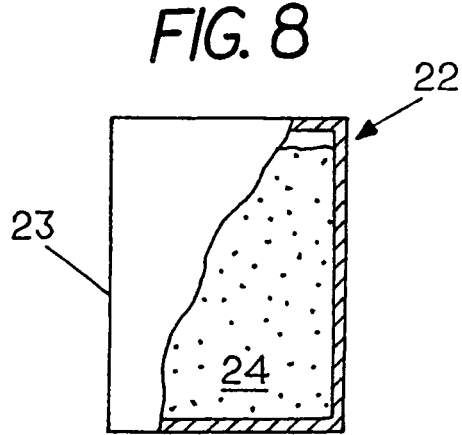
FIG. 8 shows DMH/silver based liquid sanitizer for treating a medium such as a body of water.

FIG. 8 shows a stand-alone disinfectant DMH/silver based liquid sanitizer 22 comprising a dispenser container 23 supporting a solution 24 containing a DMH/Ag/Cl complex therein. In regards to solution 24, solution 24 may be formed in various forms. For example solution 24 may be formed by directly adding the synthesized DMH/Ag/Cl complex to a volume of fluid. Solution 24 may alternatively be formed by an initial fluid containing silver chloride particles and particles of the synthesized DMH/Ag complex wherein the synthesized DMH/Ag complex interacts with the chloride from the silver chloride to form the DMH/Ag/Cl complex.

FIG. 9 shows the DMH/Ag/Cl complex solution 24 being dispensed through an orifice 25 of a dispenser container 23 into the body of water 13 supported by housing 14. Use of the DMH/Ag/Cl complex solution 24 thus will be ideal for an open body of water that requires immediate disinfection.

In further regards to the present invention, the powder, granules, dipstick, liquid, and tablets produced from the silver chloride and DMH or synthesized DMH/Ag complex are such that they may be used alone such as without the need for any secondary biocide to effectively exceed disinfection goals for recreational waters such as swimming pools, spas, and hot tubs such as, for example, providing at least a 6.0 log reduction in microorganism numbers within 0.5 minutes for *E. coli* and at least a 6.0 log reduction in microorganism numbers within 2.0 minutes for *E. Faecium* in the body of recreational water. In addition the powder, granules, dipstick, liquid, and tablets produced from the silver chloride and DMH or synthesized DMH/Ag complex are of particular utility as biocidal agents for use in other environments that may not have been previously mentioned such as industrial as well as medical and home use applications including but not limited to elements of protective coatings such as paints, hand wash formulations, in ointments and related topical applications, cosmetics, cleaning and/or disinfectant/sanitation products, toilet bowl cleaners, cooling towers, liquid paint, air washer systems, wastewater, pulp and paper processing operations, oil field applications, and decorative fountains and sanitation of recreational water such as swimming pools and spas. The synthesized DMH/Ag complex and synthesized DMH/Ag/Cl complex are also intended to be used as a component in coating fibers and filters.

Referring to FIGS. 10 and 11, FIG. 10 shows an embodiment of a stand-alone disinfectant comprising DMH/silver based water-sanitizing dispenser 38 having a housing 39 containing a compartment 40 therein. Located in compartment 40 is a source of synthesized DMH/Ag complex 41. Also located in compartment 40 is an additive such as reduced levels of halide and/or other chemicals that function to increase the efficacy of the antimicrobial activity of the synthesized DMH/Ag complex 41 in a body of water. Although various types of additives may be used, in the embodiment of FIG. 10, the additive comprises chloride ions derive from silver chloride 42. A set of openings 44 allows water access to compartment 40 and to the source of synthesized DMH/Ag complex 41 and the silver chloride 42.

FIG. 11 shows an alternative embodiment of a stand-alone disinfectant comprising DMH/silver based water-sanitizing dispenser 45 having a first housing 46 containing a compartment 47 and a second housing 48 with a compartment 49 therein. Located in compartment 47 is an additive that functions to increase the efficacy of the antimicrobial activity of the synthesized hydantoin/Ag complex such as chloride ions derive from a silver chloride 50 and located in compartment 49 is a source of synthesized DMH/Ag complex 51. A set of openings 52 allows water access to compartment 47 and to the silver chloride 50. Similarly, a set of openings 53 allows water access to compartment 49 and the source of synthesized DMH/Ag complex 51.

In regards to the source of synthesized DMH/Ag complex 41, 51 of FIGS. 10 and 11, note that FIG. 11 shows source of synthesized DMH/Ag complex 51 in particle form with the aforementioned particles having an initial size that is larger than the size of opening 53 to prevent the particles of synthesized DMH/Ag complex 51 from escaping through opening 53.

FIG. 10 shows source of synthesized DMH/Ag complex 41 in tablet form. In regards to the tablets of synthesized DMH/Ag complex 51, it is noted that various types of material, including but not limited to microcrystalline cellulose (MCC), may be used as a binder in the formation of the tablets of synthesized DMH/Ag complex 51. It is noted that the synthesized DMH/Ag complex 51 may be tabletized with the silver chloride in an alternative embodiment so that both the synthesized DMH/Ag complex 51 and the metal ion donor can be placed in the body of fluid to be treated.

A feature of the invention is that it includes a method for decreasing a level of free chlorine in a body of water to a level below a normally ineffective biocidal level of chlorine in the body of water when chlorine is used in combination with a metal ion donor. For example, one can sanitize a body of water with a source of metal ions and a source of chlorine, wherein the chlorine level in combination with the source of metal ions is selected so as to be insufficient to bring the level of microorganism in the body of water an acceptable level, for example, an at least a 6.0 log reduction in microorganism numbers within 0.5 minutes for *E. coli* and at least a 6.0 log reduction in microorganism numbers within 2.0 minutes for *E. Faecium* in the body of recreational water. By introducing a biocidal ineffective compound having a hydantoin ring therein into the body of water one can bring the level of microorganism in the body of water to an acceptable level such as an at least a 6.0 log reduction in microorganism numbers within 0.5 minutes for *E. coli* and at least a 6.0 log reduction in microorganism numbers within 2.0 minutes for *E. Faecium* in the body of recreational water.

While the use of a biocidal metal such as silver has been described one may use other sources of biocidal metal for generating biocidal metal ions into the body of water. For example, various types of biocidal metal such as zinc or copper may be used, other examples of silver biocidal metals include silver, silver alloy or some combination thereof. The biocidal metals may be introduced as metallic, zero valence material, or as metal ions that can be introduced into the water by dissolution of soluble metal salts, or by the dissolution of the metal itself. For example, silver ion can be introduced into the water through the dissolution of silver nitrate, or through the dissolution of metallic silver as the result of conversion to silver oxide and subsequent conversion of the oxide to more soluble silver species. Mixtures of different salts, or of salts with metallic material, may be combined together to provide the necessary concentration of metal ions in the water.

Thus in one example the use of a silver-hydantoin complex such as a complex formed by silver and 5,5-dimethylhydantoin ("DMH") synthesized or formed in situ to control microbial growth in a body of water such as a spa, hot tub or swimming pool while reducing or eliminating the need for secondary disinfectants such as chlorination.

In another example the sanitizing agent may include a compound having a hydantoin ring, such as glycolylurea, in conjunction with a source of metal ions in a chlorine metal ion system where the metal ions are silver ions and the compound having the hydantoin ring has been found to enhance the effectiveness in maintaining low or zero bacteria levels.

Conventionally, a halogen such as chlorine may be used as a sanitizer. While chlorine is an effective sanitizer it has unpleasant side effects including a strong odor. To limit the amount of chlorine used a second sanitizer such as a source of metal ions is used with the combination of silver ions and the chlorine to form a sanitizing agent which is effective in maintaining the bacteria count at zero. Typically, it has been found that when a second sanitizer, such as a silver ion source, is used in conjunction with the chlorine the level of free chlorine can be maintained at a minimum of 0.5 ppm to maintain the bacteria count at zero.

While the use of metal ions, such as silver ions, reduces the necessary level of chlorine to maintain the bacteria count at zero the use of a compound containing a hydantoin ring, such as dimethylhydantoin (DMH), in conjunction with the sanitizer reveals the level of chlorine can be reduced even further while still maintaining the bacteria count at zero. Although DMH is not a sanitizer the DMH may make the silver more active and effective in bacteria control thereby lessening the need for chlorine and the unpleasant side effects of chlorine as well as reducing the cost of chlorine to maintain a bacteria count of zero.

EXAMPLE

A 32,000 gallon outdoor pool was sanitized using commercially available FROG™ minerals and chlorine. The FROG™ Minerals included silver chloride on a limestone carrier. In addition to the conventional sanitizing treatment using silver chloride and chlorine sufficient DMH was added to the pool to bring the DMH content of the pool to a level of about 10 ppm to 12 ppm DMH in the pool. The free chlorine, total chlorine, pH and the bacteria in the pool were monitored over a three month period. During the period both humans and animals swam in the pool. Periodic testing revealed that while the total chlorine ranged from 1 ppm to 4 ppm the free chlorine ranged from about 0.1 ppm to about 1 ppm with an average of about 0.5 ppm. Testing revealed that the total bacteria count was zero even though the measured levels of free chlorine was as low as 0.1 ppm.

As described above the addition of a compound, such as DMH, which contains in the molecule at least one hydantoin ring, with the typical following skeletal structure

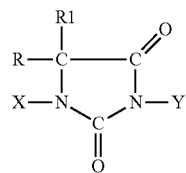

was found effective to lessening the need for one to maintain higher levels of a halogen such as chlorine in water sanitizing systems that use halogens and metal ions to sanitize the system.

Thus, in one aspect the invention includes a sanitizing agent for maintaining a biocidal effective bacteria count wherein the sanitizing agent comprises a halogen; a metal ion donor for donating a metal ion; and a compound containing a hydantoin ring with the combination thereof enhancing the effectiveness of the sanitizing agent to enable maintaining the bacteria level less than if either the halogen and the metal ion donor were used without the compound containing the hydantoin ring.

While a number of compounds with a hydantoin ring may be used one may want to avoid those compounds where the group on the compound may have an adverse effect on the purpose of the sanitation product. For example, compounds with groups that have adverse effect on human skin should be avoided if the sanitizing agent is used in a body of water such as a swimming pool or a hot tub, while such compounds may be used with those bodies of water which are sanitized and do not come into contact with humans.

Examples of other well known compounds wherein the molecule in the compound contains the hydantoin ring structure include 1-bromo-3-chloro-5,5dimethylhydantoin (BCDMH), 1,3 dichloro-5,5 dimethylhydantoin (DCDMH), ?Silver dimethylhydantoin (AgDMH), 1-hydroxymethyl-5, 5-dimethlyl hydantoin, glycolyurea and Copper hydantoin, Hydantoin-5-acetic acid, and Imidazolidines including parabanic acid, 2-Thiohydantoin, hydantoin purum, hydantoin, 1-Aminohydantoin hydrochloride, 2-Imidazolidone, 2-Imidazolidone purum, 2-Imidazolidinethione, 2-hydrazino-2-imidazoline hydrobromide, 2-oxo-1-imidazolidinecarbonyl chloride, 1-methylhydantoin, 5-methylhydandtoin, 2-imidazolidone-4-carboxylic acid, allantoin, allantoin purum, creatinine anhydrous, creatinine biochemika, creatinine hydrochloride, 2-methyl-2-imidazoline, 2-methylthio-2-imdazoline hydrodide, 3-brmo-1-chlor-5-5-dimethlyhydantoin, 1-3-dibromo-5,5-dimethlyhydantoin purium, 1-3-dichlorol-5,5-dimethylhydantoin, 1,3-dichlor-5, 5-dimethylhydantoin, hydantoin-5-acetic acid. 2-chlorocarbonyl-1-methanesulfonyl-2imidazolidinone. 5,5-dimethylhydantoin purum. 5,5-dimethylhydantoin, 2-imino-1-imidaolidineacetic acid, 1,3-dimethyl-2-imidazolidinone puriss, 1,3-dimethly-2-imidazolidinone purum, 1,3-dimethyl-2-imidazolidinone, 1-(2-hydroxyethyl)-2-imdazolinone, 1,5,5-trimethlylhydantoin, 5-ethyl-5-methylhydantoin, 2-phenyl-2-imidazoline purum, 2-(4,5-dihydro-1h-imidazoyl)-2-phenol, 4-(4,5-dihydro-1H-imidazol-2yl)phenylamine, 5-methyl-5-phentylhydantoin, 2-benzylimidazoline, 4-(4-methyl-4,5-dihydro-1H-imidazol-2-yl)phenyl, Imidazolidinyl urea, 4-hydroxymephenytoin, triethoxy-3-(2-imidazolin-1-yl)propysiliane purum, 1,(p-tosyl)-3,4,4-trimethylimidazolidine, naphazoline nitrate purisss, 5,5,diphenyl-2-thiohydantoin, 5-(4-hydroxyphenyl)-50phenylhydantion, 5-(p-methyl phenyl)-5-phenyhydantoin, 1,3,bisbensyl-2-oxoimidazoline-4,5-dicarboxylic acid. Other examples of hydantoins are listed in European patent EP0780125 which is hereby incorporated by reference. The above list of compounds with a hydantoin ring is illustrative and no limitation thereto is intended.

In one example of the invention a silver-hydantoin complex, either formed in situ or synthesized, is used to control microbial growth in a body of non recreational water or recreational water such as a spa, hot tub or swimming pool and in some instances may even eliminate the need for a halogen companion such as chlorine. In another example the compound having a hydantoin ring may be added to a medium such as a body of water to reduce or eliminate the need for chlorination when a halogen such as chlorine is used in conjunction with metal ions to sanitize a medium. The sanitizing agent may be used in solid form where the sanitizing agent includes both a source of metal ions and a compound containing a hydantoin ring.

In other examples the invention is a sanitizing agent in a tablet or granular form for maintaining a biocidal effective bacteria count with the sanitizing agent comprising a halogen, a metal ion donor for donating a metal ion donor, and a compound containing a hydantoin ring with the combination thereof enhancing the effectiveness of the sanitizing agent to enable maintaining the bacteria level less than if the halogen and the metal ion donor were used alone. The metal ion donor may comprise silver chloride and the halogen may comprise chlorine where the chlorine is a liquid, a gas or a solid. A biocidal effective bacteria count, which is zero, can be obtained by using a compound containing a hydantoin ring such as dimethlyhydantoin (DMH), which lacks any independent biocidal properties.

One aspect of the invention is a method of decreasing a level of free chlorine below a normally ineffective biocidal level of chlorine in a body of water containing a source of metal ions and a source of chlorine yet maintaining a biocidal effective bacteria count by introducing a biocidal ineffective compound having a hydantoin ring therein into the body of water. In some cases the compound containing a hydantoin ring is introduced to a sanitizer containing a metal ion donor and a halogen. The method may include sanitizing by maintaining a level of free silver at least 20 ppb and a level of a compound containing a hydantoin ring of at least 10 ppm while maintaining the level of free chorine of at least 0.2 ppm in bodies of recreational water such as a swimming pool, spas hot tubs or the like.

One may have a dispenser containing a sanitizing agent in solid or liquid form wherein the sanitizing agent includes a biocidal ineffective compound containing a hydantoin ring wherein the biocidal ineffective compound enhances the effectiveness of the sanitizing agent as the sanitizing agent is dispensed from the dispenser. By biocidal ineffective compound it is meant that the compound when used alone lacks biocidal properties that would reduce or eliminate microorganisms.

In one example the antimicrobial agent for use in killing and controlling microorganisms in a body of recreational water the antimicrobial agent contains a source of silver metal ions where the source of silver is either silver or silver chloride and a source of unhalogenated or halogenated hydantoins is selected from the group consisting of DMH, BCDMH, and AgDMH with the antimicrobial agent releasing silver metal ions and hydantoins into the open body of water to provide an at least a 6.0 log reduction in microorganism numbers within 0.5 minutes for *E. coli* and at least a 6.0 log reduction in microorganism numbers within 2.0 minutes for *E. Faecium* in the body of recreational water. The antimicrobial agent may comprises a stand-alone disinfectant tablet wherein the disinfectant tablet includes a nonantimicrobial additive (DMH) to help increase the efficacy of the antimicrobial activity of the antimicrobial agent hydantoin/silver ion complex and the source of silver metal ions includes either silver chloride or colloidal silver. The antimicrobial agent may be in either liquid or nonliquid form and the nonliquid form may be a solid for example a powder, granules or tablet. The source of silver metal ions may comprise a substrate coated or impregnated with metallic silver. The source of unhalogenated hydantoin may be selected from the group consisting of 5,5-dimethylhydantoin (DMH), silver hydantoin (AgDMH) and the source of halogenated hydantoin or from a halogenated group consisting of bromochlorodimethylhydantoin (BCDMH) and dichlorodimethylhydatoin (DCDMH) and the antimicrobial agent may be secured to the carrier. The carrier may comprise a dispenser or a stick with one end of the stick including a handle to enable one to immerse the antimicrobial agent into a body of water.

Examples of the invention include antimicrobial agents where the source of silver metal ions and the source of hydantoins may comprise a stand-alone tablet with a synthesized DMH/silver complex. In some cases the source of silver metal ions, the hydantoins, and the additive comprises a synthesized DMH/silver/chloride complex and in some cases the additive may comprises a chlorine donor.

The invention also includes a method of safeguarding a body of water from an inadvertent halogen deficiency, such as chlorine deficiency, for example a chlorine level below 2 ppm where adding the compound containing the hydantoin ring to the body of water releases additional metal ions into the body of water wherein the halogen and the metal ion must normally provide an at least a 6.0 log reduction in microorganism numbers within 0.5 minutes for *E. coli* and at least a 6.0 log reduction in microorganism numbers within 2.0 minutes for *E. Faecium* in the body of water. If the chlorine level falls below 2 ppm, which is the normal level of chlorine to maintain the body of water in the above condition, one can supplement the system without adding more chlorine by adding a hydantoin or a halogenated hydantoin to the body of water wherein the hydantoin is added in quantity to enhance the effectiveness the halogen system in the event the available chlorine falls below 2 ppm. The metal ion, which is released to kill harmful microorganisms may be a silver ion. The silver ion may be released from a silver ion donor and examples of a silver ion donor include silver chloride, metallic silver, silver alloys or combinations thereof. Examples of body of recreational water may include a swimming pool, a hot tubs or a spa where the level of chlorine can often be maintained as low as about 0.1 ppm while still maintaining the body of water in a sanitized condition by use of the invention described herein.

In one aspect the invention includes an antimicrobial agent for use in killing and controlling microorganisms in a body of recreational water wherein the antimicrobial agent contains a source of silver metal ions a halogen and a source of unhalogenated or halogenated hydantoins, the antimicrobial agent normally maintaining a halogen level and a silver ion level in the body of water effective to control bacteria wherein the antimicrobial agent may be either, a liquid, a solid, a powder or a mixture thereof and the halogen may be either chlorine or bromine.

In one example the invention may include a body of water containing an antimicrobial agent and a nonantimicrobial agent wherein the nonantimicrobial agent enhances the antimicrobial activity of the antimicrobial agent and the body of water is a body of recreational water, which may be a swimming pool, hot tub or spa.

A feature of the invention is that it may include a method of maintain the level of microorganisms in a body of water at safe levels for human use by supplying a first disinfectant (chlorine) in the body of water wherein the level of first disinfectant is insufficient to maintain the body of water suitable for recreational use, supplying a second disinfectant (silver ions) in the body of water wherein the level of the second disinfectant and the level of the first disinfectant either alone or in combination is insufficient to maintain the body of water suitable for recreational use, and enhancing the effectiveness of first disinfectant and the second disinfectant by adding DMH to the body of water to bring the level of microorganism in the body of water an at least a 6.0 log reduction in microorganism numbers within 0.5 minutes for *E. coli* and at least a 6.0 log reduction in microorganism numbers within 2.0 minutes for *E. Faecium* in the body of recreational water.

The first or second disinfectant may be supplied in either, liquid, solid or powder form, which may be supplied from a dispenser that is hand held or is placed in the body of water.

In other examples the invention may include the method of maintaining a body of water suitable for recreational use wherein the chlorine level is normally maintained in a range between 0.1 ppm and 0.5 ppm by adding silver ions and DMH to the body of water wherein examples of body of water comprise a swimming pool, a spa or a hot tub wherein the body of water includes silver ions and DMH and the body of water includes chlorine in amounts between 0.1 ppm and 0.5 ppm.

The invention may include a system for rendering a body of water suitable for external use comprising a dispenser containing a source of silver ions, a dispenser containing a source of chlorine, and a dispenser containing a source of DMH where single or multiple dispensers are used.

The invention may also include a method of killing microorganism in a body of water by adding chlorine to the body of water sufficient to maintain the free chlorine level at half the total chlorine level.

In other examples the invention may comprise a stand-alone disinfectant tablet for use in killing and controlling microorganisms in a body of water, which includes a source of silver metal ions, an unhalogenerated or halogenated hydantoin capable of forming a complex with the silver ions in the body of water and a halogen additive where the halogenated hydantoin comprises for example BCDMH. Examples of stand-alone disinfectant tablet may include a layer of silver chloride encapsulating an exterior surface of the tablet and the source of silver metal ions, the source of hydantoins, and the additive comprise a synthesized DMH/silver/chloride complex or the source of silver metal ions and the source of hydantoins comprise a synthesized DMH/silver complex and the halogen additive comprises either chlorine or a chlorine donor. The disinfectant may comprise multiple layers of silver chloride and multiple layers of a synthesized DMH/Ag complex and the carrier may comprise a synthesized DMH/Ag/Cl complex.

Examples of the invention include a stand-alone disinfectant pellet for use in killing and controlling microorganisms in body of recreational water comprising a carrier having an exterior surface, a water penetrable adhesive forming a water penetrable matrix on the exterior surface of the carrier, a source of silver metal ions dispersed within the adhesive water penetrable matrix and a source of unhalogenated or halogenated hydantoins dispersed within the adhesive water penetrable matrix. The silver metal-hydantoins containing matrix coated carrier releasing silver metal ions into the body of recreational water to kill microorganisms when contacted by the body of recreational water and also releasing the hydantoins when contacted by the body of recreational water containing silver metal ions. In this example the hydantoins forming a complex with the silver ions to kill microorganisms in the body of recreational water by being an additive to help increase the efficacy of the antimicrobial activity of a hydantoins/silver ion complex. For example the combination being effective in providing at least a 6.0 log reduction in microorganism numbers within 0.5 minutes for E. coli and at least a 6.0 log reduction in microorganism numbers within 2.0 minutes for E. Faecium in the body of recreational water, which is a common EPA acceptable limit for bodies of recreational water such as pools, spas and hot tubs. In these examples the source of silver metal ion may be in a tablet and the source of silver metal ion may comprise silver chloride and the additive may include a chloride donor. The stand-alone disinfectant solid may be a pellet, a tablet a plurality of granules, a powder or mixtures thereof and may include a source of unhalogenated hydantoin comprising 5,5-dimethylhydantoin (DMH) and the source of halogenated hydantoin comprise bromochlorodimethylhydantoin (BCDMH) and dichlorodimethylhydatoin (DCDMH). The stand-alone disinfectant pellet may include the silver metal-hydantoins containing matrix coated carrier housed in a container and the carrier comprises a source of unhalogenated or halogenated hydantoins. The source of silver metal ions and the source of hydantoins in the pellet may be a synthesized DMH/silver complex or a synthesized DMH/silver/chloride complex and the source of silver metal ions may comprise a metallic silver alloy.

The invention may include a stand-alone disinfectant liquid for use in killing and controlling microorganisms in a fluid such as a body of recreational water comprising a confined volume of water, a source of silver metal ions located in the water to kill microorganisms, a source of unhalogenated or halogenated hydantoins located in the fluid, the source of unhalogenated or halogenated hydantoins releasing the hydantoins when contacted by the biocidal metal ions in the fluid, the hydantoins forming a complex with the silver ions effective in killing microbial in the water, and an additive to help increase the efficacy of the antimicrobial activity of a hydantoins/silver ion complex effective in providing at least a 6.0 log reduction in microorganism numbers within 0.5 minutes for E. coli and at least a 6.0 log reduction in microorganism numbers within 2.0 minutes for E. Faecium in the body of recreational water. The source of silver metal ions may comprise metallic silver, silver chloride, a metallic silver alloy or pure silver. The source of unhalogenated hydantoin, for example, may comprise 5,5-dimethylhydantoin (DMH) and the source of halogenated hydantoin may comprise bromochlorodimethylhydantoin (BCDMH) and dichlorodimethylhydatoin (DCDMH). The source of silver metal ions and the source of hydantoins may comprise a synthesized DMH/silver complex or a synthesized DMH/silver/chloride complex and the additive may comprises a chloride donor. In some examples the fluid may comprise water or may contain water.

The invention may include a stand-alone disinfectant powder for use in killing and controlling microorganisms in a body of recreational water comprising a source of silver metal ions for killing microorganisms in the body of recreational water, a source of unhalogenated or halogenated hydantoins, the source of unhalogenated or halogenated hydantoins releasing the hydantoins when contacted by the body of recreational water containing silver metal ions, the hydantoins forming a complex with the silver ions to kill microorganisms in the body of recreational water; and an additive to help increase the efficacy of the antimicrobial activity of a hydantoins/silver ion complex to be effective in providing at least a 6.0 log reduction in microorganism numbers within 0.5 minutes for E. coli and at least a 6.0 log reduction in microorganism numbers within 2.0 minutes for E. Faecium in the body of recreational water. The source of silver metal ions and the source of unhalogenated or halogenated hydantoins may be in solid form such as tablets or granules and the source of silver metal ions may comprises metallic silver, silver chloride, metallic silver, silver alloys or pure silver. The source of an unhalogenated hydantoin may comprise 5,5-dimethylhydantoin (DMH) and the source of halogenated hydantoin comprise bromochlorodimethylhydantoin (BCDMH) and dichlorodimethylhydatoin (DCDMH). The source of silver metal ions and the source of hydantoins may comprise a synthesized DMH/silver complex or a synthesized DMH/silver/chloride complex and the additive may comprises a chloride donor.

The invention may include a stand-alone dispenser for killing microorganisms in a body of recreational water comprising a first housing having a water accessible compartment containing a source of silver metal ions and a source of an additive to help increase the efficacy of the antimicrobial activity of the hydantoins/silver ion complex, the source of silver metal ions releasing silver metal ions and the source of an additive release the additive into the body of recreational water when contacted by the body of recreational water; and a second housing having a water accessible compartment containing a source of unhalogenated or halogenated hydantoins for releasing the hydantoins when contacted by the body of recreational water containing silver metal ions with the hydantoins forming a complex with the silver ions effective in providing at least a 6.0 log reduction in microorganism numbers within 0.5 minutes for E. coli and at least a 6.0 log reduction in microorganism numbers within 2.0 minutes for E. Faecium in the body of recreational water. The source of silver metal ions may comprise silver chloride and the source of additive may comprise silver chloride. The source may comprise unhalogenated 5,5-dimethylhydantoin a 5,5-dimethylhydantoin (DMH) and the source of halogenated hydantoins may includes bromochlorodimethylhydantoin (BCDMH) and dichlorodimethylhydatoin (DCDMH). The second housing and the first housing may be located in a dispenser having a set of openings for the ingress and egress of water into the compartments in the dispenser. The source of silver metal ions may comprises a metallic silver alloy, pure silver, silver chloride, silver alloys and may be a substrate coated or impregnated with metallic silver.

In addition to the above examples of hydantoins one may wish to use other compounds which containing a hydantoin ring as described hereinabove.

The invention claimed is:

1. A method for maintaining a body of water in a sanitized condition comprising:
    maintaining the chlorine level in the body of water at a level of between 0.1 ppm and 0.5 ppm;
    introducing a source of metal ions into the body of water wherein the chlorine level in combination with the source of metal ions is selected so as to be insufficient to sanitize the body of water; and
    introducing a biocidal ineffective compound having a hydantoin ring therein into the body of water to increase the concentration of soluble metal ions in the body of water whereby the combination of the chlorine and the metal ions sanitize the body of water.

2. The method of claim 1 wherein the halogen level comprises a chlorine level and the source of metal ions comprises a source of silver ions wherein a combination thereof is unable to bring the level of microorganism in the body of water to an at least a 6.0 log reduction in microorganism numbers within 0.5 minutes for *E. coli* and at least a 6.0 log reduction in microorganism numbers within 2.0 minutes for *E. Faecium* in the body of recreational water; and the introducing of the biocidal ineffective compound having a hydantoin ring therein into the body of water brings the level of microorganism in the body of water to an at least a 6.0 log reduction in microorganism numbers within 0.5 minutes for *E. coli* and at least a 6.0 log reduction in microorganism numbers within 2.0 minutes for *E. Faecium* in the body of water.

3. The method of claim 1 wherein adding the biocidal compound comprises adding an unhalogenated compound containing a hydantoin ring or a halogenated compound in either tablet, pellet or granular form or combinations thereof.

4. The method of claim 1 wherein sanitizing to maintain a biocidal effective level of halogen by adding a compound containing a hydantoin ring to a sanitizing agent containing a metal ion donor and a halogen.

5. The method of claim 1 wherein introducing the biocidal ineffective compound generates a level of free silver of at least 20 ppb and a level of a compound containing a hydantoin ring of at least 10 ppm.

6. A method of maintaining a body of water suitable for recreational use wherein the chlorine level is maintained in a range between 0.1 ppm and 0.5 ppm, which is insufficient to render the water suitable for recreational use, and adding to the body of water a silver ion source and a compound containing an unhalogenated hydantoin ring to render the water suitable for recreational use while maintaining the chlorine level between 0.1 ppm and 0.5 ppm.

7. The method of claim 6 wherein the compound containing the unhalogenated hydantoin ring is a tablet containing DMH.

8. The method of claim 6 wherein the compound containing the unhalogenated hydantoin ring is a solid that is either a tablet, a pellet, a plurality of granules or a mixture thereof.

9. The method of claim 8 wherein the tablet comprises a source of silver ions in a layer of the tablet with at least a portion of the layer having an exposed surface for contact in the body of water.

10. A method for maintaining a body of water in a sanitized condition comprising:

maintaining a chlorine level of between 0.1 ppm and 0.5 ppm in the body of water;

placing a solid in tablet or granular form in the body of water with the solid comprising a metal ion source and a compound having an unhalogenated hydantoin ring;

releasing metal ions and the unhalogenated hydantoin ring into the water;

forming a soluble complex of at least the metal and the unhalogenated hydantoin in the body of water;

wherein the soluble complex of silver inhibits the formation of insoluble metal compounds.

11. The method of claim 10 wherein the source of metal ions comprises a source of silver ions and the compound containing the hydantoin ring and the source of silver ions are separate.

12. The method of claim 10 wherein the source of metal ions comprises a source of silver ions and the compound containing the hydantoin ring lacks any independent biocidal properties.

* * * * *